United States Patent
Bouzid et al.

(10) Patent No.: US 9,366,630 B2
(45) Date of Patent: Jun. 14, 2016

(54) FLUORESCENCE IMAGING AUTOFOCUS SYSTEMS AND METHODS

(71) Applicant: LI-COR, Inc., Lincoln, NE (US)

(72) Inventors: Ahmed Bouzid, Lincoln, NE (US); Chris Lesiak, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 0 days.

(21) Appl. No.: 14/480,258

(22) Filed: Sep. 8, 2014

(65) Prior Publication Data

US 2016/0069808 A1    Mar. 10, 2016

(51) Int. Cl.
*G01N 21/64* (2006.01)
*G02B 17/06* (2006.01)
*G02B 13/22* (2006.01)
*G02B 21/16* (2006.01)
*G02B 21/36* (2006.01)

(52) U.S. Cl.
CPC ............ *G01N 21/6458* (2013.01); *G02B 13/22* (2013.01); *G02B 17/0605* (2013.01); *G02B 21/16* (2013.01); *G02B 21/361* (2013.01); *G01N 2021/6463* (2013.01); *G01N 2201/06113* (2013.01); *G01N 2201/1053* (2013.01)

(58) Field of Classification Search
CPC ..... G02B 21/365; G01N 21/64; G01N 21/59; G01N 21/47
See application file for complete search history.

(56) References Cited

U.S. PATENT DOCUMENTS

| 4,761,071 | A | | 8/1988 | Baron | |
|---|---|---|---|---|---|
| 4,978,861 | A | * | 12/1990 | Sabater | ................ G01B 11/303 250/559.23 |
| 5,608,527 | A | * | 3/1997 | Valliant | ................ G01B 11/303 356/445 |
| 6,917,696 | B2 | | 7/2005 | Soenksen | |
| 7,015,445 | B2 | | 3/2006 | Bishop | |
| 7,457,446 | B2 | | 11/2008 | Soenksen | |
| 7,518,652 | B2 | | 4/2009 | Olson et al. | |
| 7,993,927 | B2 | | 8/2011 | Frangioni | |
| 2003/0010930 | A1 | * | 1/2003 | Thorwirth | .......... G01N 21/6452 250/458.1 |
| 2014/0098364 | A1 | * | 4/2014 | Ahner | .................... G01N 21/47 356/237.2 |
| 2014/0104409 | A1 | | 4/2014 | Bishop | |

OTHER PUBLICATIONS

Michel Doucet et al. Microscope with 3D Mapping Capabilities for Planetary Exploration Applications, Proceedings of SPIE, vol. 8550, Dec. 18, 2012.
European Patent Office, European Search Report, Feb. 5, 2016.

* cited by examiner

*Primary Examiner* — Kiho Kim
(74) *Attorney, Agent, or Firm* — Leydig, Voit & Mayer, Ltd; Gerald T. Gray

(57) ABSTRACT

Quantitative fluorescence imaging systems and methods using angular illumination to obtain automatic focus information. Laser scanning (e.g., point or line scanning) with angular illumination in combination with an area imaging sensor, such as with a bi-telcentric scanner, is used to determine sample height (relative to a detection axis orthogonal to a platform holding the sample) and also correct for sample height in subsequent scans.

19 Claims, 6 Drawing Sheets

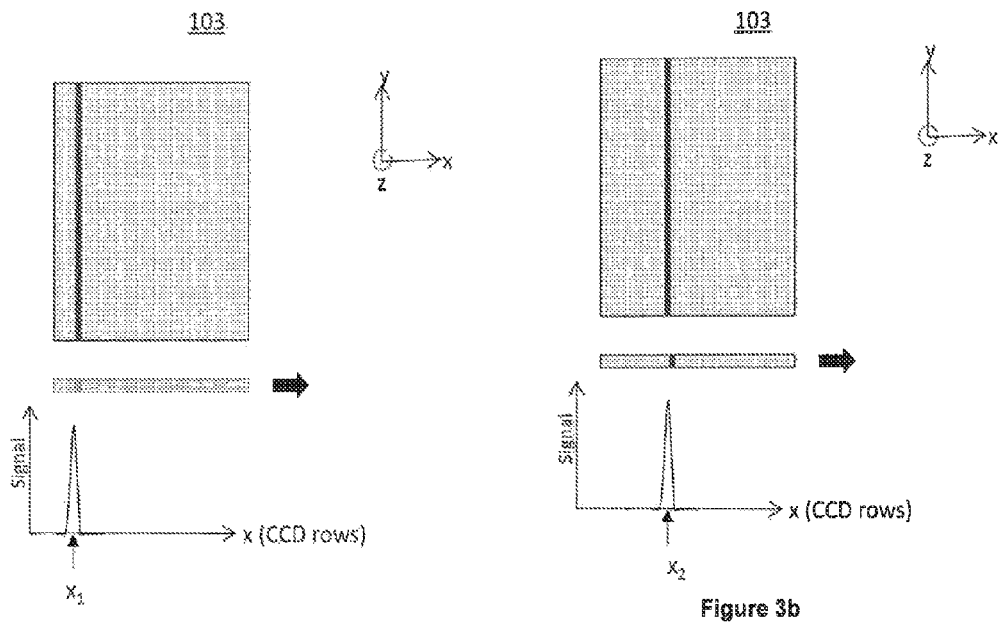
Figure 3a
Figure 3b
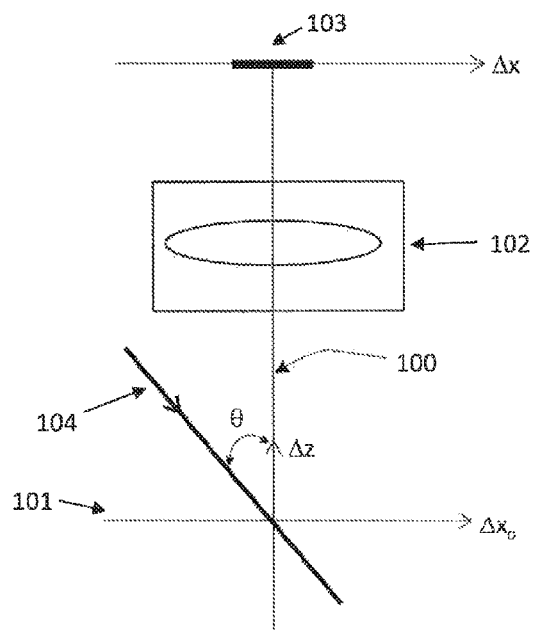
Figure 4

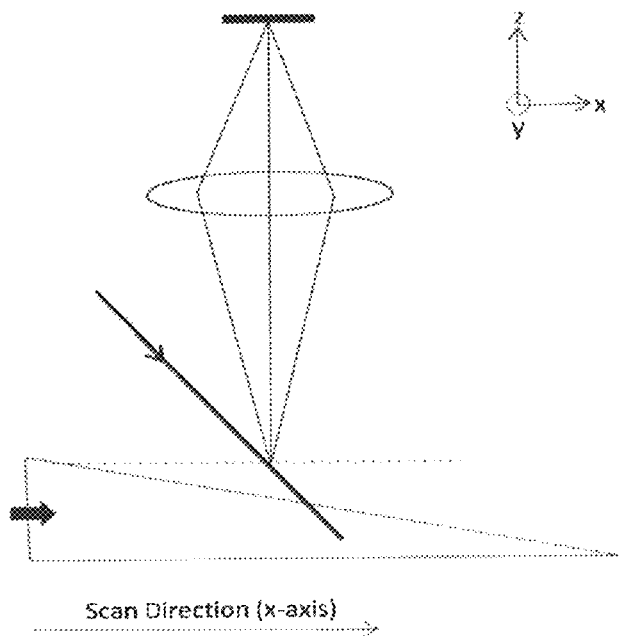
Figure 5
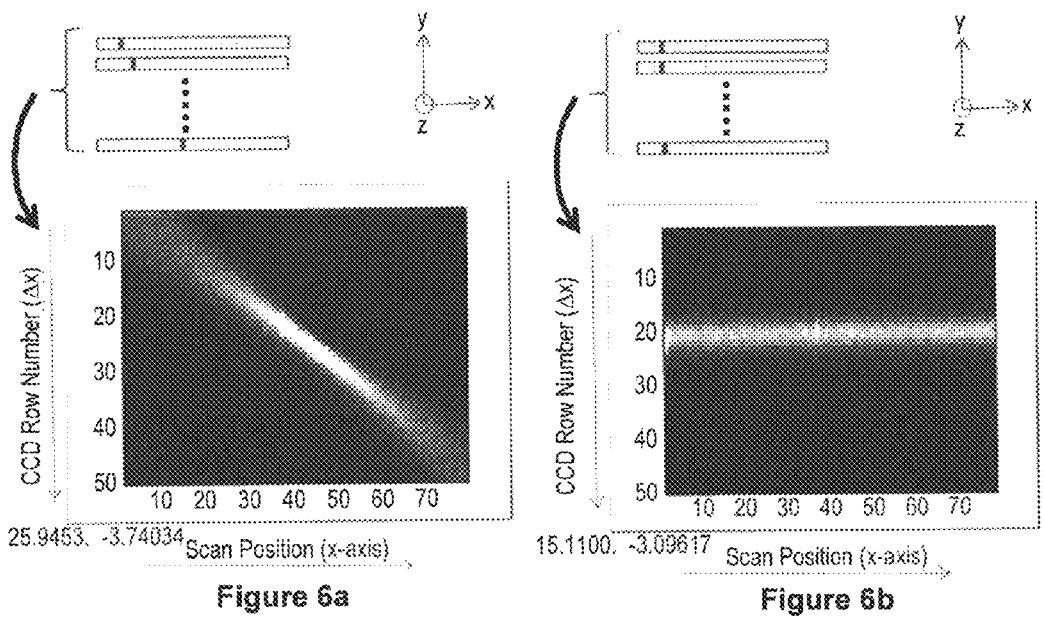
Figure 6a
Figure 6b

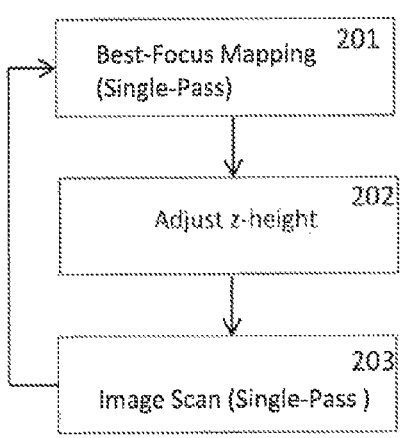
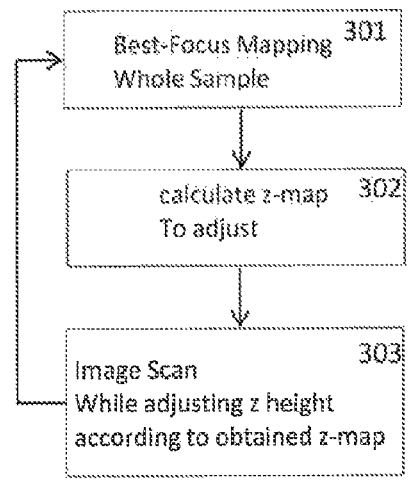
Figure 7a
Figure 7b

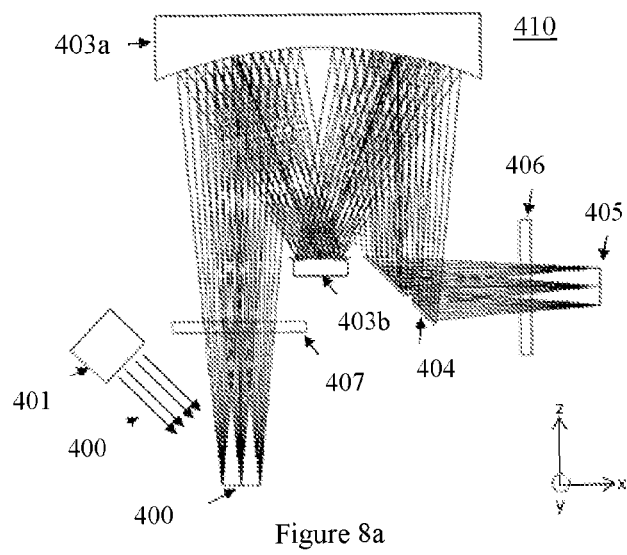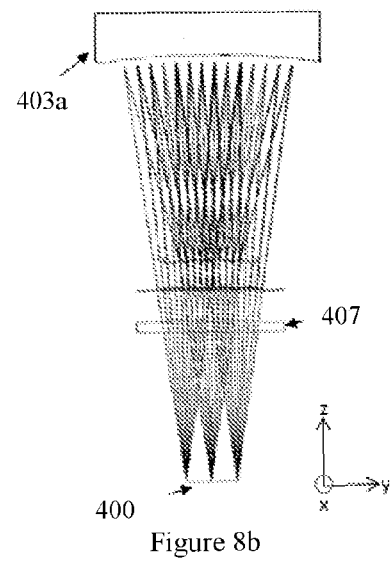
Figure 8a
Figure 8b

FLUORESCENCE IMAGING AUTOFOCUS SYSTEMS AND METHODS

BACKGROUND

The present disclosure relates to quantitative fluorescence imaging and more specifically to an autofocus system and method using angular illumination.

A recent improvement in fluorescence imaging is a bi-telecentric, wide-field fluorescence scanner that allows for accurate quantification measurements with focus-independent pass-to-pass registration. U.S. patent application Ser. No. 14/312,409, filed Jun. 23, 2014, titled "Telecentric, Wide-Field Fluorescence Scanning Systems and Methods," which is hereby incorporated by reference for all purposes, discusses features of a bi-telecentric, wide-field fluorescence scanning system. One feature of such a design is angular illumination (excitation), which has the benefit of reduced optical background and therefore higher sensitivity. A down side of angular illumination, however, is that as the height of the sample changes, the location of the imaged line on the sensor changes as well. Therefore, in order to fully take advantage of this angular illumination feature, it is important to track where the excitation light hits the sample as its height changes.

Another feature that the bi-telecentric scanner can use is a differential scan imaging technique to achieve high image performance by subtracting background signal from a non-illuminated area from the signal detected from an illuminated area. U.S. patent application Ser. No. 13/084,371 filed Apr. 11, 2011, titled "Differential Scan Imaging Systems and Methods," which is hereby incorporated by reference for all purposes, discusses useful differential scan imaging techniques. When using such techniques, combined with angular illumination, it is desirable that the z-height of the fluorescence sample be constant relative to the scanner system. If the sample height changes, the detected signal from the illuminated area 'walks off' across the detection array and therefore the amount of signal measured is not accurate. Therefore, with a given stationary detector array in place, it is important to correct for sample height changes before actual imaging data is collected.

Olsen et al. (U.S. Pat. Nos. 7,518,652, 7,646,495, and 7,893,988, which are each hereby incorporated by reference) devised ways to focus a line scan camera prior to and during the capture of imagery data from a specimen on a microscope slide. The approach taken consists of computing focus information prior to scanning the slide. This focus information is taken in a point focus or ribbon-focus procedure. In the point focus case, the line scan camera system first positions the slide at a desired measurement location, moves the objective lens through a predefined set of height values, and acquires imagery data at each height and then determines the height (z-axis setting) of maximum contrast, which in turn is established as the optimal focus height. With the ribbon-focus procedure, the objective is continuously moved in a sinusoidal fashion as the slide is in scanning motion. Imagery data are analyzed and heights of maximum contrast determine the best focus z-heights. The two procedures differ in how the vertical motion of the objective lens is synchronized with the horizontal motion of the slide during image acquisition. The first method, which can be described as a 'stop-and-go' method, is slow as there is quite a bit of overhead time as a result of the stop-and-go process. The ribbon-focus method is much faster, but still takes more than 1 min for a 15 mm×15 mm scan area.

Olsen's method was devised for microscopic imaging where illumination light comes through the microscope objective, i.e. co-axial or non-angular relative to the imaging path. This means that as the vertical distance between the objective and sample changes (z-axis), the location on the imaging sensor, in the x-y plane, does not change—just image contrast changes. In this microscope configuration, it does make sense to adjust the objective position to different height locations and finding the best position with the image having the highest contrast. However, with angular illumination, the x-y location on the imaging sensor does change as the focus changes. This means that additional steps to find the x-y location would be needed before Olsen's 'stop-and-go' process of finding best focus can be implemented. An even more elaborate set of steps would be needed for the strip-focus method. This adds complication and slows the process even further.

Furthermore, Olsen's technique has no provisions for the detected signal walking off on the detector as a result of z-height changes of the sample. Therefore, the idea of taking images at different heights does not work because at many z heights there would be no signal to detect (walked off the detector) and thus any contrast-based scheme would fail to detect where the best focus is. It is therefore necessary to bring the sample height near the nominal height that gives best focus first so it can be measured correctly, e.g., using Differential Scan Imaging techniques.

Therefore, there is still a need for a more robust, quantitative, fast macroscopic fluorescence imager that does not have the limitations of angular dependence on where in the field the light originates from. Furthermore, there is still a need to accurately maintain the relative locations of the origins of fluorescence light on the sample so that multi-pass images are aligned accurately and thus eliminate the focus dependent positional shifting present in current macroscopic wide-field imagers.

SUMMARY

The present disclosure relates to quantitative fluorescence imaging and more specifically to wide-field fluorescence imaging systems and methods using angular illumination to obtain automatic focus information.

The present embodiments use laser scanning (e.g., point or line scanning) with angular illumination in combination with a detector array, such as with a bi-telecentric scanner, which advantageously overcome the difficulties and deficiencies associated with previous autofocus schemes. This present embodiments provide a significantly faster and simpler process to track the height locations of where angular illumination light intercepts a sample, e.g., fluorescing sample.

According to an embodiment, a fluorescence imaging system is provided that typically includes a sample platform for holding a fluorescent material, a light detector having an array of sensing locations for detecting light emitted from the fluorescent material, and an optical imaging system positioned between the sample platform and the light detector and configured to focus light emitted from field points on the sample platform onto the light detector, wherein contiguous field points on the sample platform are simultaneously imaged onto contiguous sensing locations on the light detector. The imaging system also typically includes an illumination system including a light source that emits excitation light in an absorption band of the fluorescent material, wherein the illumination system provides a beam of illumination that impinges on the fluorescent material at an angle relative to a detection axis, wherein a plane of incidence of the beam includes the detection axis and the scan direction. The imaging system also typically includes a scanning mechanism that enables continuous scanning of the beam of illumination relative to the sample platform along the scan direction, and an intelligence module (e.g., one or more processors) coupled to the light detector and configured to determine variations along the scan direction of a height of the fluorescent material parallel to the detection axis based on variations along the scan direction of positions on the light detector of maximum illuminance (e.g., fluorescence or excitation scatter) detected by the light detector.

In certain aspects, the scanning mechanism rescans the beam of uniform illumination along the scan direction, e.g., in an imaging mode, and the imaging system includes a mechanism for adjusting a position of the platform as the scanning occurs based on the determined variations in height of the fluorescent material so as to compensate for the determined variations in height of the fluorescent material. In certain aspects, the system includes a memory attached to the intelligence module for storing a height map of the fluorescent material on the platform based on, or including, the determined variations.

In certain aspects, the optical imaging system comprises a bi-telecentric optical imaging system. In certain aspects, the bi-telecentric optical imaging system includes an Offner relay mirror system arrangement comprising a first mirror element having a spherical mirror surface and a second mirror element having a spherical mirror surface, wherein the entry aperture stop and the exit aperture stop each comprise a portion of the first mirror element. In certain aspects, the first mirror element presents a convex-shaped mirror surface, and the second mirror element presents a concave-shaped mirror surface. In certain aspects, the bi-telecentric optical imaging system comprises a bi-telecentric lens arrangement, wherein the entry aperture stop includes a first refractive lens element and wherein the exit aperture stop includes a second refractive lens element.

In certain aspects, the scanning mechanism adjusts one of the sample platform along the scan direction or the light detector and illumination beam along the scan direction. In certain aspects, the beam of illumination has one of a spot shaped profile and a line-shaped profile. In certain aspects, for a beam having a line-shaped profile, the beam of illumination is substantially uniform along its length or the beam has a brightness or intensity profile that is substantially Gaussian.

In certain aspects, contiguous field points on the sample platform are simultaneously imaged onto contiguous sensing locations on the light detector. In certain aspects, the light detector includes a CCD array detector or other light detector or sensor.

According to another embodiment, a method is provided for imaging a fluorescent material that absorbs light in an absorption band of wavelengths and that emits fluorescent light in an emission band of wavelengths. The method typically includes illuminating the fluorescent material on the sample platform with an illumination beam having excitation light in the absorption band, the beam of illumination impinging on the fluorescent material at an angle relative to a detection axis, wherein a plane of incidence of the beam includes the detection axis and the scan direction and scanning the illumination beam along the scan direction. The method also typically includes detecting emissions from the first portion of fluorescent material using a detector system including a light detector having an array of sensing locations, and an optical imaging subsystem positioned between the sample platform and the light detector and configured to focus light emitted from field points on the sample platform onto the light detector, wherein contiguous field points on the sample platform are simultaneously imaged onto contiguous sensing locations on the light detector, and determining variations along the scan direction of a height of the fluorescent material parallel to the detection axis based on variations along the scan direction of positions on the light detector of maximum illuminance detected by the light detector.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 3a and FIG. 3b show examples of images registered by an array detector from a laser line impinging on the sample using the fluorescence imaging scanner of FIG. 1.

FIG. 4 shows various relationships in the fluorescence imaging scanner of FIG. 1 according to one embodiment.

FIG. 5 shows an example of using a fluorescence imaging system of FIG. 1 with a tilted slide according to another embodiment.

FIG. 6a shows an example of brightest signals on the detector array when a laser line scans across the tilted slide and along the scan axis according to an embodiment.

FIG. 6b shows an example of brightest signals on the detector array when height compensation is used according to an embodiment.

FIG. 7a shows an example of an image scan process according to an embodiment.

FIG. 7b shows an example of an image scan process according to another embodiment; and FIGS. 8a and 8b show examples of a fluorescence imaging system including an Offner relay mirror system.

DETAILED DESCRIPTION

To image in fluorescence, a target (e.g., containing fluorescent material) is illuminated by an optical signal having a first spectral content (excitation light) where a portion of such a signal is absorbed by at least part of the target and re-emitted as optical signal of a second spectral content (emission light). The emission light is then detected by a detection system as a measure of the amount present of that target at that location. Imaging a fluorescently labeled area, therefore, requires excitation light delivered to the target area, an imaging system that collects light from the target area and projects it onto an optical detector (e.g., detector array), and a means to separate the emitted fluorescence light from the portion of excitation light that makes its way through the imaging system. The latter, typically, includes one or more interference filters.

Wide-Field imaging, as considered herein, includes collecting light from a contiguous area and projecting it onto a detector array, such as a CCD or other detector having an array of sensing locations or pixels, at the same time in a way that preserves the relative locations of each point within the contiguous area. This is different from collecting light from one point at a time and sequentially scanning to a different point in order to cover a larger area, i.e. point scan imaging. It is also different from collecting light from a large area and condensing the total amount of light onto a detector and reading it as total signal. The latter is common for many measurement techniques that do not require specific location information.

One skilled in the art will understand that other types of useful sensors or detectors and arrays of sensors, such as CCD and CMOS sensors can be used. Other useful sensors might include photodiodes, avalanche photodiodes, silicon photomultiplier devices, an array of photomultiplier tubes, a focal plane array, etc.

Figure 1:
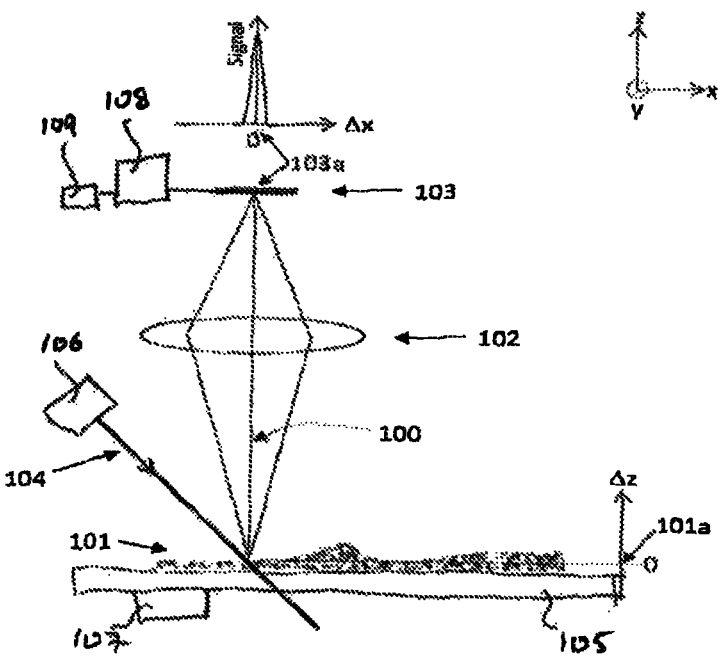
FIG. 1 shows a side view of components of a fluorescence imaging scanner, with a laser beam incident on a sample at an angle in the x-y plane relative to an imaging optical axis, according to an embodiment.
Figure 2:
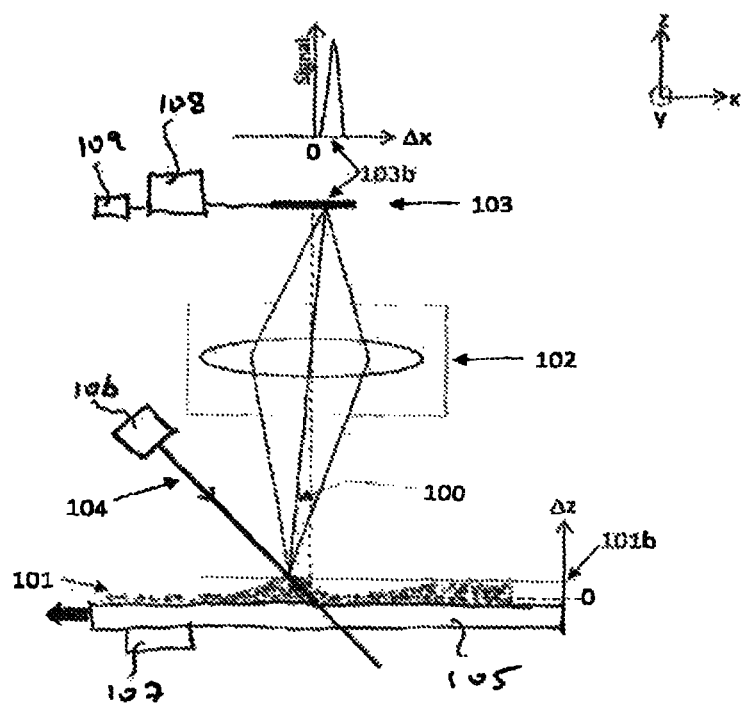
FIG. 2 shows a side view of components of the fluorescence imaging scanner of FIG. 1, with the laser beam incident on the sample at an angle in the x-y plane relative to an imaging optical axis, but impinging on the sample at a different z-height, according to an embodiment.

FIG. 1 shows a fluorescence imaging scanner according to an embodiment. An excitation beam 104 is incident on target sample 101 at an angle in the x-z plane relative to the imaging optical axis 100. (It should be appreciated that directions are arbitrary and that orthogonal x-y-z directions are shown for simplicity of discussion.) The target sample may be located on a sample platform 105, which may be substantially planar, or may have some surface contour. In FIG. 1, fluorescently labeled target sample 101 is on top of a substantially planar sample platform or medium (e.g., a slide) and can cover the whole x-y surface area on the platform or a portion of the platform. Beam 104 crosses the imaging axis 100 at a height 101a, in the z-direction. When the sample is in focus, as is shown in FIG. 1, light collected from sample 101 by imaging system 102 is refocused onto an array detector 103. When laser beam 104 intercepts sample 101 at z-height 101a, the maximum collected signal at detector array 103 is located at position 103a along the x-direction on the array. When the height of the point where the laser beam 104 intercepts sample surface 101 changes, the location along the x-direction on the detector array changes. This is shown in FIG. 2, where sample 101 is moved along the x-axis such that the laser beam hits a point on the sample surface with z-height 101b, different from 101a. As a result, the maximum collected signal at detector array 103 is located at position 103b along the x-direction on the array. By detecting the location of 103b relative to 103a, the z-height difference between 101b and 101a can be directly determined and therefore the sample 101 z-location can be changed so that the maximum collected signal at detector array 103, 103b, is moved to 103a. Beam 104 may be a spot beam or a laser line. In general, the angle of the illumination is such that a plane of incidence of the beam 104 includes the detection axis and the scan direction.

An illumination system 106, including a light source, generates excitation light beam 104 that illuminates a portion of the sample 101. The light source may include a laser source (e.g., diode laser or other laser source), an LED, a broadband lamp, etc, and appropriate optional optical elements to shape the light beam as desired. The excitation light beam 104 may be configured to illuminate an area on the sample for spot imaging applications, or it may be configured to illuminate a line on the sample for line scanning applications. In both spot imaging and line imaging applications, scanning can be achieved by moving the illumination light across the target area while the detection system and the target remain fixed, for example, using a scanning mirror or similar element that sequentially aims the illumination beam at different target locations over time and the detection system is accordingly aimed at these locations. As another example, scanning can be achieved using scanning mechanism 107, e.g., by moving (e.g., via conventional motors and linear actuators as are well known) the sample platform 105 relative to a fixed illumination beam and a fixed detection system, or by moving both the illumination and detection systems while holding the sample platform 105 fixed.

FIGS. 3a and 3b show examples of images registered by detector array 103 from a laser line, with its length along the y-axis, incident on sample 101 at two different z heights (and same angle of illumination). The first height results in the imaged line located at row number $x_1$, along the x-direction, and the second z-height causes that imaged line to move to a different row number $x_2$. Therefore, a detection of the location of the brightest signal along the x-direction on the detector array (row numbers, for example) is a direct measure of the z location of the fluorescing surface. This relation can be represented as follows [see, FIG. 4]:

$$\Delta z(x) = -\frac{\Delta x_o(x)}{\tan\theta} = -\frac{M}{\tan\theta}\Delta x(x) \quad [1]$$

where θ is the angle incident illumination beam 104 makes with the imaging optical axis 100. M is the magnification relationship between sample 101 and detector array 103. For example, M=+1 for an Offner imaging system used in one embodiment of the bi-telecentric scanner. Thus, at any x-position along the scan axis, the z-height change relative to a nominal, best-focus, z-location can be directly measured by detecting the row location shift of the brightest signal on the detector array. This then can be followed by adjusting the sample height position so that the brightest signal location would be at the nominal, best focus location. An imaging scan pass is then taken with the fluorescing surface at the best-focus height location and thus achieve both the best contrast (sharpness) and highest signal. U.S. patent application Ser. No. 14/312,409, which is incorporated by reference herein, discusses aspects of Offner imaging systems and telecentric imaging, which are useful in certain embodiments herein. Briefly, telecentric imaging refers to the case where the chief rays from all the points being images are parallel to each other. A design can be telecentric in the object space where the Principal or chief rays are parallel to each other in the space between the 1$^{st}$ element of the imaging optics and the sample. On the other hand, a design that's telecentric in the image space has its Principal or chief rays between the last element of the imaging optics and the detector array parallel to each other. A benefit of telecentricity is that when the distance in a telecentric space changes, for example between imaging lens 102 and the detector 103, then the distance between the chief rays at the detector 103 remains unchanged.

An Offner relay system includes optical lens elements and/or mirror elements that create a bi-telecentric imaging system. For example, an Offner mirror system has a primary mirror element and a secondary mirror element that together create a bi-telecentric 1:1 imaging system that approaches perfect imaging. Primary and secondary mirror elements each present a generally spherical mirror surface, at least where light interacts with each element. This design leverages the symmetry present in this mirror system to create both object-space and image-space telecentric areas, enabling placement of both a rejection filter and an emission filter without sacrificing any light collection capability or imaging performance. The magnification of this imaging technique, and therefore location accuracy, is quite insensitive to focus errors and therefore image-to-image or pass-to-pass registration is very robust. A benefit of an Offner relay mirror system is its reflective nature and therefore it is achromatic which makes it ready for combining more than one color without the need for any color related adjustments or corrections.

Examples of useful filters include notch filters to block most of the excitation light and band-pass filters to further block any residual excitation light leaking through the notch filter.

FIG. 5 shows an example of using an embodiment with a severely tilted platform, e.g., microscope slide. FIG. 6a shows the location of the brightest signal on the detector array as the platform is scanned along the scan axis (x-axis). It shows that this location shifts across the detector array rows. By converting the change in row location of brightest signal, Δx, to a change in z-height of the slide according to equation 1, a map of the required z-height adjustment is obtained so that the brightest detected signal does not walk-off the rows in the CCD array used for detecting the signal. FIG. 6b shows the result obtained when this compensation is implemented. As is shown, the CCD row-number of where the brightest signal is stays constant and therefore the imaging after that adjustment is at the best-focus of the imaging system and the collected signal is not affected by the fact that the slide was severely tilted to begin with.

FIGS. 7a-b show two examples of implementing a pre-scan, brightest-signal mapping and subsequent adjustment of sample z-height to correct for the change in sample z-height according to an embodiment. In FIG. 7a, a z-height map is obtained (201) for each pass and the sample height is adjusted (202) before the image scan (203) for that pass is effectuated. In one embodiment, one average z-height adjustment is made, but more than one point adjustment per pass can also be implemented for even finer corrections. This method advantageously requires that no additional passes need be made; the pre-scan z mapping can be obtained while the sample is going to the start position of the scan (fly-forward). The data collection needed for this is much faster than the mechanical speed of moving the slide. A best-focus mapping (201) and therefore the needed z-height adjustment for the whole width of a microscope slide (2.5 cm pass) can be obtained in less than 1 sec (typically limited by the mechanical speed to home the slide). The adjustment needed (202) takes less than 0.1 sec at most, in the case of one average adjustment, and no additional time at all for the case where z-adjustment is made during the scan data is collected. Advantageously, there is no need to stop-and-go or to perform additional pre-scan passes with z-adjustments.

FIG. 7b shows another case of z-height mapping before image scan is performed. In this case, a number of fast passes are made, again typically limited by mechanical speeds only, to height variation across the whole sample, then a 'whole sample' z-height map (301) can be calculated (with interpolation, for example) and specific places to adjust sample height at are determined (302). The adjustment in this case can be done during the Image Scan (303). The total time added to scanning the whole microscope slide (7.5 cm×2.5 cm) with this approach is about 10 sec, again limited only by available mechanical speeds. In certain embodiments, the collected z-height data is stored to a memory.

It should be appreciated that various other ways can be adopted to implement the essence of this invention, including mapping sample height (e.g., z-heights), adjusting sample and/or imaging system heights, and collecting data at or near best focus locations.

FIGS. 8a and 8b show a front view and side view, respectively, of a fluorescence imaging system 410 according to one embodiment. Fluorescence imaging system 410 as depicted includes an Offner relay mirror system having a primary mirror element 403a and a secondary mirror element 403b that together create a bi-telecentric 1:1 imaging system that approaches perfect imaging. Mirror elements 403a and 403b each present a generally spherical mirror surface, at least where light interacts with each element. This design leverages the symmetry present in this mirror system to create both object-space and image-space telecentric areas, enabling placement of both a rejection filter 407 and an emission filter 406 as depicted without sacrificing any light collection capability or imaging performance. For example, as shown, rejection filter 407 is positioned in the object-space telecentric area and the emission filter 406 is placed in the image-space telecentric area. In this manner all filtering is done with chief rays parallel to each other and distances between chief rays is unchanged when adjusting focus. The magnification of this imaging technique, and therefore location accuracy, is quite insensitive to focus errors and therefore image-to-image or pass-to-pass registration is very robust. The aperture stop defines the size of the cone of light collected by or admitted to the optical system. As shown in FIG. 8a, mirror element 403b acts as both the entry aperture stop and the exit aperture stop. That is, the object-space telecentric area is created or exists in the light path between the sample platform 400 and the portion of mirror element 403b defining the entry aperture stop, and the image-space telecentric area is created or exists in the light path between the detector 405 and the portion of mirror element 403b defining the exit aperture stop. The aperture stop is also where the chief rays pass through its center, i.e., cross the optical axis (for mirrors, light changes direction after it hits a mirror); mirror element 403b is where chief rays hit in the center (optical axis of that mirror). In certain aspects, rejection filter 407 includes one or more filter elements that reject (or filter out) excitation light wavelengths, while allowing other light wavelengths as desired to pass. Similarly, emission filter 406 includes one or more filter elements that allow emission band wavelengths to pass, while rejecting other wavelengths as desired. Examples of useful filters include notch filters to block most of the excitation light and band-pass filters to further block any residual excitation light leaking through the notch filter.

Referring to FIG. 8a, a light source 401 generates an excitation light beam 402, preferably nearly collimated, that illuminates a portion of the sample area 400. Light source 401 may include a laser source (e.g., diode laser or other laser source), an LED, a broadband lamp, etc., and appropriate optional optical elements to shape the light beam as desired. The excitation light beam 402 may be configured to illuminate an area on the sample for area imaging applications as depicted, or it may be configured to illuminate a line on the sample for line scanning applications. From every point on the sample area 400 being imaged, there is a cone of light 408 that includes a chief ray at its center that passes through rejection filter 407 in a telecentric way, the chief ray is refocused by Offner mirror elements 403a and 403b to the image side where the chief ray passes through emission filter 406 also in a telecentric way before it reaches detector array 405, also perpendicularly to it, in a telecentric way. Optional folding mirror 404 is used to redirect the path for ease of packaging. FIG. 8b shows that imaging is telecentric in the y-z plane as well. With this imaging system, a strip area can be imaged in fluorescence under fully telecentric filtering conditions. Larger sample areas are covered by scanning the sample platform or the imaging system to other different areas and stitching all images together to produce a uniform, contiguous image of the desired total area.

Figure 9B:
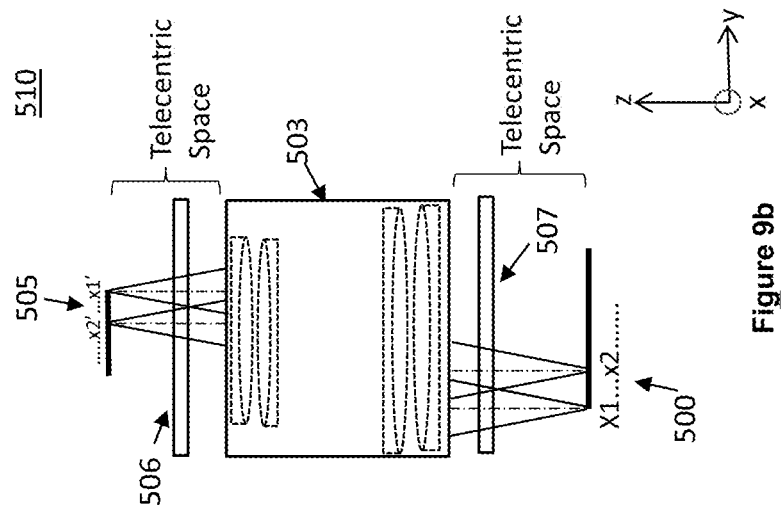
FIGS. 9a and 9b show examples of a fluorescence imaging system including a bi-telecentric imaging system.
Figure 9A:
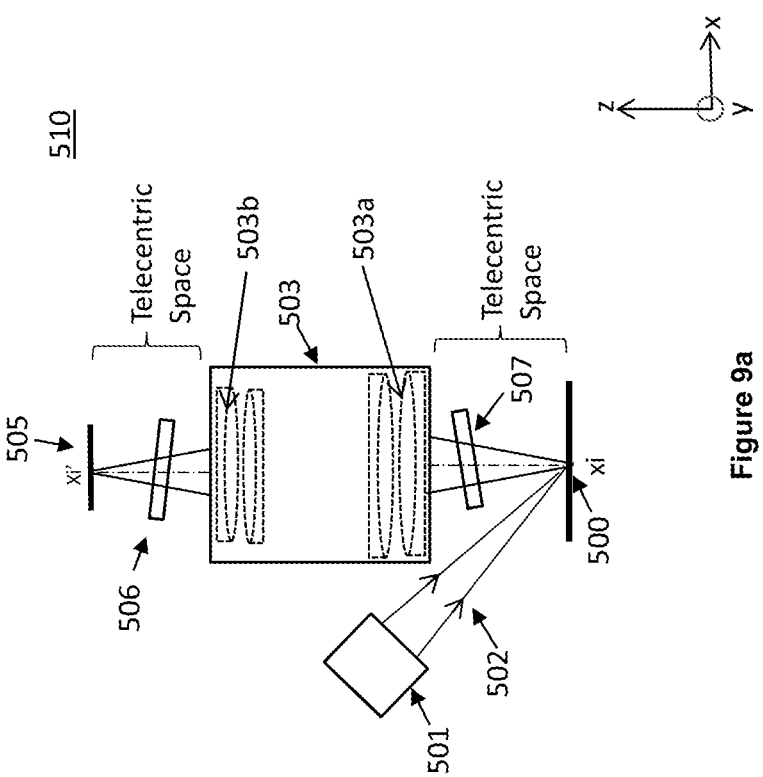

FIGS. 9a and 9b show a front view and side view, respectively, of a fluorescence imaging system 510 according to an embodiment. Fluorescence imaging system 510 as depicted includes a bi-telecentric lens-based optical imaging system 503 having a first refractive lens element 503a and a second refractive lens element 503b. Lens element 503a includes an entry aperture stop wherein a telecentric space is created between target platform 500 and lens element 503a. Similarly, lens element 503b includes an exit aperture stop wherein a telecentric space is created between lens element 503b and detector 505. Both aperture stops can be the same or similar. A rejection filter 507 is positioned in the object-space telecentric area and the emission filter 506 is placed in the image-space telecentric area. In this manner all filtering is done with chief rays parallel to each other and distances between chief rays is unchanged when adjusting focus.

It should be understood that the first refractive lens element and the second refractive lens element can each include more than one lens element. It should also be understood that the first aperture stop and the second aperture stop can each be in air, or located before all the lenses within the first and second refractive lens elements, respectively, or somewhere in the middle of the first and second refractive lens elements, respectively, or after all the lenses within the first and second refractive lens elements, respectively. For example, a lens element within a refractive lens element may include an aperture stop.

In certain embodiments, an intelligence module 108 (FIGS. 1, 2), such as one or more processors, is communicably coupled with the detector, e.g., detector 103. The intelligence module 108 is adapted to receive and process signals from the detector, e.g., signals representing, or proportional to, the detected illumination within the detector's detection bandwidth. The intelligence module 108 may also be coupled with the illumination system 106 and scanning mechanism 107 for controlling operation of these systems. The intelligence module 108 may automatically process the data and signals as received, or it may receive the data and signals, store the signals to memory 109, and process subsequently, e.g., in response to a user command. An optional display device (not shown) is provided in certain embodiments to display data representative of various signals and images captured and/or processed by the detector and/or intelligence module. A memory module or device can also be provided to store data and code for use by the intelligence module, or for another system. For example, the memory may store code, executable by one or more processors, for implementing methods as disclosed herein, and/or data from the detectors and/or processor may be stored thereon. The memory may include any non-transitory medium such as a RAM or ROM, hard disk or any portable medium such as a DVD or CD.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A fluorescence imaging system, comprising:
  a sample platform for holding a fluorescent material;
  a light detector having an array of sensing locations for detecting light emitted from the fluorescent material;
  an optical imaging system positioned between the sample platform and the light detector and configured to focus light emitted from field points on the sample platform onto the light detector, wherein contiguous field points on the sample platform are simultaneously imaged onto contiguous sensing locations on the light detector;
  an illumination system including a light source that emits excitation light in an absorption band of the fluorescent material, wherein the illumination system provides a beam of illumination that impinges on the fluorescent material at an angle relative to a detection axis, wherein a plane of incidence of the beam includes the detection axis and a scan direction, wherein the scan direction is perpendicular to the detection axis;
  a scanning mechanism that enables continuous scanning of the beam of illumination relative to the sample platform along the scan direction; and
  an intelligence module coupled to the light detector and configured to determine variations along the scan direction of a height of the fluorescent material parallel to the detection axis based on variations along the scan direction of positions on the light detector of maximum illuminance detected by the light detector.

2. The imaging system of claim 1, further including a memory attached to the intelligence module for storing a height map of the fluorescent material on the platform.

3. The imaging system of claim 1, wherein the optical imaging system comprises a bi-telecentric optical imaging system.

4. The imaging system of claim 3, wherein the bi-telecentric optical imaging system comprises an Offner relay mirror system arrangement comprising a first mirror element having a spherical mirror surface and a second mirror element having a spherical mirror surface, wherein an entry aperture stop and an exit aperture stop each comprise a portion of the first mirror element.

5. The imaging system of claim 4, wherein the first mirror element presents a convex-shaped mirror surface, and wherein the second mirror element presents a concave-shaped mirror surface.

6. The imaging system of claim 3, wherein the bi-telecentric optical imaging system comprises a bi-telecentric lens arrangement, wherein an entry aperture stop includes a first refractive lens element and wherein an exit aperture stop includes a second refractive lens element.

7. The imaging system of claim 1, wherein the scanning mechanism adjusts one of the sample platform along the scan direction or the light detector and illumination beam along the scan direction.

8. The imaging system of claim 1, wherein the light source comprises a diode laser and wherein the light detector comprises a CCD array detector.

9. The imaging system of claim 1, wherein the beam of illumination has one of a spot shaped profile and a line-shaped profile.

10. The imaging system of claim 1, wherein the scan direction is parallel to the sample platform.

11. A method of determining height variations of a fluorescent material on a sample platform, wherein the fluorescent material absorbs light in an absorption band of wavelengths and emits fluorescent light in an emission band of wavelengths, the method comprising:
  a) illuminating the fluorescent material on the sample platform with an illumination beam having excitation light in the absorption band, the beam of illumination impinging on the fluorescent material at an angle relative to a detection axis, wherein a plane of incidence of the beam includes the detection axis and a scan direction, wherein the scan direction is perpendicular to the detection axis;
  b) scanning the illumination beam along the scan direction;
  c) detecting emissions from the first portion of fluorescent material using a detector system including a light detector having an array of sensing locations, and an optical imaging subsystem positioned between the sample platform and the light detector and configured to focus light emitted from field points on the sample platform onto the light detector, wherein contiguous field points on the sample platform are simultaneously imaged onto contiguous sensing locations on the light detector; and
  d) determining variations along the scan direction of a height of the fluorescent material parallel to the detection axis based on variations along the scan direction of positions on the light detector of maximum illuminance detected by the light detector.

12. The method of claim 11, wherein scanning includes moving one or both of a) the sample platform, and b) the illumination beam and the light detector along the scan direction.

13. The method of claim 11, wherein the scan direction is parallel with a surface defined by the sample platform.

14. The method of claim 11, further including storing to a memory a height map of the fluorescent material on the platform.

15. The method of claim 11, further including rescanning the beam of illumination along the scan direction and adjusting a position of the platform as the scanning occurs based on the determined variations in height of the fluorescent material so as to compensate for the determined variations in height of the fluorescent material.

16. The method of claim 11, wherein the optical imaging system comprises a bi-telecentric optical imaging system.

17. The method of claim 11, wherein the light source comprises a diode laser and the light detector comprises a CCD array detector.

18. The method of claim 11, wherein the illumination beam has one of a spot shaped profile and a line-shaped profile.

19. A fluorescence imaging system, comprising:
  a sample platform for holding a fluorescent material;
  a light detector having an array of sensing locations for detecting light emitted from the fluorescent material;
  an optical imaging system positioned between the sample platform and the light detector and configured to focus light emitted from field points on the sample platform onto the light detector, wherein contiguous field points on the sample platform are simultaneously imaged onto contiguous sensing locations on the light detector;
  an illumination system including a light source that emits excitation light in an absorption band of the fluorescent material, wherein the illumination system provides a beam of illumination that impinges on the fluorescent material at an angle relative to a detection axis, wherein a plane of incidence of the beam includes the detection axis and a scan direction, wherein the scan direction is perpendicular to the detection axis;
  a scanning mechanism that enables continuous scanning of the beam of illumination relative to the sample platform along the scan direction; and
  an intelligence module coupled to the light detector and configured to determine a difference in height of the fluorescent material at an imaging location on the sample platform relative to a previous imaging location based on a distance along the scan direction between positions on the light detector of a maximum illuminance detected by the light detector at the imaging location and the previous imaging location.

* * * * *